United States Patent [19]

McGuire et al.

[11] Patent Number: 5,366,457
[45] Date of Patent: Nov. 22, 1994

[54] METHOD AND APPARATUS FOR PREPARING A BONE AND TENDON GRAFT

[75] Inventors: David A. McGuire, 3418 Lakeside Dr., Anchorage, Ak. 99515; Stephen D. Hendricks, Anchorage, Ak.

[73] Assignee: David A. McGuire, Anchorage, Ak.

[21] Appl. No.: 19,525

[22] Filed: Feb. 19, 1993

Related U.S. Application Data

[63] Continuation-in-part of Ser. No. 806,906, Dec. 13, 1991, Pat. No. 5,257,996.

[51] Int. Cl.⁵ .............................. A61F 5/00; A61F 2/32
[52] U.S. Cl. ............................................ 606/86; 606/96
[58] Field of Search .............. 606/102, 103, 104, 105, 606/96, 97, 98, 86, 87, 88, 79, 80

[56] References Cited

U.S. PATENT DOCUMENTS

| | | | |
|---|---|---|---|
| 2,301,500 | 11/1942 | Anderson | 606/103 |
| 2,697,433 | 12/1954 | Zehnder | 606/103 |
| 4,235,428 | 11/1980 | Davis | 606/96 |
| 4,257,411 | 3/1981 | Cho | 128/92 EB |
| 4,421,112 | 12/1983 | Mains | 606/96 |
| 4,462,395 | 7/1984 | Johnson | 128/92 B |
| 4,524,766 | 6/1985 | Petersen | 128/92 H |
| 4,721,104 | 1/1988 | Kaufman et al. | 128/92 VW |
| 4,781,182 | 11/1988 | Purnell et al. | 128/92 VD |
| 4,787,377 | 11/1988 | Laboureau | 128/92 VD |
| 4,822,362 | 4/1989 | Walker et al. | 623/20 |
| 4,823,780 | 4/1989 | Odensten et al. | 128/92 VD |
| 4,862,882 | 9/1989 | Venturi et al. | 128/92 VD |
| 4,901,711 | 2/1990 | Goble et al. | 606/98 |
| 4,920,958 | 5/1990 | Walt et al. | 606/96 |
| 4,946,462 | 8/1990 | Watanabe | 606/148 |
| 4,985,032 | 1/1991 | Goble | 606/96 |
| 5,002,545 | 3/1991 | Whiteside et al. | 606/80 |
| 5,037,426 | 8/1991 | Goble et al. | 606/96 |
| 5,078,719 | 1/1992 | Schreiber | 606/96 |
| 5,122,144 | 6/1992 | Bert | 606/96 |
| 5,192,321 | 3/1933 | Strokon | 623/13 |
| 5,242,444 | 9/1993 | MacMillan | 606/96 |

FOREIGN PATENT DOCUMENTS 384098 8/1990 European Pat. Off. .
495487 7/1992 European Pat. Off. .

OTHER PUBLICATIONS

Cazenave, A. et al., "Reconstruction isometrique du ligament croise anterieur, Determination pre et per-operatoire du point femoral, (Isometric reconstruction of the anterior cruciate ligament. Pre and per operative determination of the isometric points)" Revue de *Chirurgie Orthopedique*, vol. 76, Paris, Masson, pp. 288–292 (1990).

Good, L. et al., "Precision in reconstruction of the anterior cruciate ligament, A new positioning device compared with hand drilling," *Acta Orthop.*, vol. 58, Scand., pp. 658–661 (1987).

Lindstrand, A. et al., "The Lund Drill Guide, An Instrument for Repair or Reconstruction of the Cruciate Ligaments," *Archives of Orthopaedic and Traumatic Surgery*, vol. 99, Verlag, J. F. Bergmann, pp. 231–233 (1982).

(List continued on next page.)

Primary Examiner—Michael A. Brown
Attorney, Agent, or Firm—Bromberg & Sunstein

[57] ABSTRACT

A bone block drill guide and a method for preparing a bone plug and tendon graft in which the bone block drill guide is used in drilling a hole through the bone plug. A harvested bone plug and tendon graft is inserted into a trough in a bone block drill guide. A drill bit is inserted through a hole in a drill guide member to accurately drill a hole in the bone plug supported in the trough below. The bone block drill guide may have a plurality of troughs of different widths. A drill guide member has a hole therethrough for guiding a drill bit. The drill guide member is aligned with a trough so that the hole in the guide member is aligned with the hole in the bottom surface of the trough.

17 Claims, 11 Drawing Sheets

OTHER PUBLICATIONS

Schmidt-Ramsin, E., "Plastik des vorderen Kreuzbandes mit freiem Transplantat mit Hilfe eines neuen Zielgerates (A New Drill Guide for Plastic Repair of the Anterior Cruciate Ligament by a Free Ligamenteous Graft)," *Archives of Orthopaedic and Traumatic Surgery*, vol. 91, Verlag, J. F. Bergmann, pp. 149–152 (1978).

Hutter, C. G. et al., "The Intramedullary Compression Rod," *Clinical Orthopaedics and Related Research*, vol. 122, pp. 165–172 (1977).

Mattheck, C. et al., "Ein neues Zielgerat unde zwei neue Kreuzbandanker zur Befestigung von prothetischem Kreuzbandersatz am Femur, (A New Drilling Device and New Anchors for the Fixation of Prosthetic Cruciate Ligaments to the Femur)," *Biomedizinische Technik Band*, vol. 36, pp. 20–23 (1991).

"The Paramax ACL Guide System Surgical Technique," brochure, Linvatec Corporation, Largo, Fla.

METHOD AND APPARATUS FOR PREPARING A BONE AND TENDON GRAFT

This application is a continuation in part of United States patent application Ser. No. 07/806,906, filed Dec. 13, 1991 now Pat. No. 5,257,996. This related application is hereby incorporated herein by reference.

BACKGROUND OF THE INVENTION

The present invention is directed to the preparation of a bone plug and tendon graft, in particular, a patella tendon bone autograft.

A common procedure for performing anterior cruciate ligament (ACL) reconstruction involves the use of a central third patella tendon graft. A bone tendon bone graft is harvested. It is then desirable to drill holes in the bone plugs (also called bone blocks) of the graft. The holes are used to thread a suture in one end and a wire in the other end. The suture and wire are for the purpose of locating the graft in the tibial and femoral tunnels. The drilling of these holes has conventionally been accomplished free hand on a platform, which may be PVC coated to have a surface texture of a coarse whetstone. There is a potential in performing such free hand drilling for the surgeon to become injured. The thumb and index finger of the surgeon are holding the bone block during the drilling and are thus in close proximity to the drill. The drill bit could potentially slip off the bone and pierce the gloves of the surgeon. This would transfer patient tissue to the surgeon's finger or thumb via the drill bit wound. A further disadvantage of performing the drilling on the platform is that the drill bit could pierce the PVC, grab some of it and subsequently pass the PVC into the hole in the bone thus contaminating the bone.

Drilling a hole in the block of a graft is difficult to get right when done freehand. If the hole is drilled too far from the end of the bone block, it may disrupt the ACL reconstruction. A suture or wire inserted through the hole is used to pull the bone block through a bone tunnel. If the hole is too far from the end, the bone block may toggle or rotate about the wire in the hole when pulled. This would make it difficult to pull the bone block into the tunnel. Similarly, this difficulty may be encountered if the hole is drilled off-center. Another problem with freehand drilling is that the graft can slip out of the surgeon's fingers and wrap around the drill. This may lead to fracture of the bone block or the graft may slip onto the floor increasing chances of contamination.

SUMMARY OF THE INVENTION

The present invention achieves accurate, controlled and simple drilling while protecting the surgeon's fingers from the drill bit and isolating the drill and bone block from the tabletop. In one embodiment, the present invention is directed to a method for preparing a bone plug and tendon graft that makes use of a bone block drill guide. A bone plug and tendon graft are harvested from the patient. The harvested bone plug is passed through a sizing tube to test the size of the plug. The harvested bone plug is inserted into a positioning station on a bone block drill guide according to the present invention. A drill guide member suspended over the bone block has a hole through which the drill is passed for drilling the hole through the bone plug. Once the hole has been drilled in the bone plug, a suture or wire may be passed therethrough. The bone block drill guide may be used to assist in repositioning the bone block in the positioning station and drilling a second hole therein.

The bone block drill guide of the present invention includes a base plate having a plurality of troughs of different widths. In each of the troughs there is at least one receiving hole therein. A drill guide member having at least one hole is supported over the trough so that the hole in the drill guide member can be aligned with the reclining hole in the trough of the base plate. A hole is drilled by inserting the bone block in a trough and aligning the drill guide member over the bone block. The drill bit is passed through the hole in the drill guide member and into the bone plug. The drill bit bores the bone plug into the receiving hole aligned with the hole in the drill guide member. Thus when the drill is used to drill a hole through the bone block, it enters a corresponding receiving hole in the bone block drill guide so as not to pick up any stray material from the base plate. The bone block drill guide may be provided with a stop clip that permits easy repositioning of the bone block beneath the drill guide member.

By using the bone block drill guide of the present invention, holes can be drilled through a bone plug accurately and with reduced risk to the surgeon's fingers. Other objects and advantages of the present invention will be more readily understood by consideration of the following detailed description taken along with the accompanying drawings.

BRIEF DESCRIPTION OF THE DRAWINGS

FIG. 6b is a side view of the drill guide member shown in FIG. 6a.

FIG. 6c is a bottom view of the drill guide member shown in FIG. 6a.

DETAILED DESCRIPTION OF THE PREFERRED EMBODIMENTS

A bone-patellar tendon-bone autograft is used in anterior cruciate ligament reconstruction surgery. By taking the graft from the patient being treated the problems of procurement of grafts, potential rejection and AIDS are avoided. The procedure may be routinely done as an outpatient surgery. The incisions may be small and cosmetically pleasing and the procedure is usually completed with tourniquet times under one hour. The procedure allows diagnostic arthroscopy and the surgeon is not committed to the anterior cruciate ligament reconstruction unless it is confirmed by the arthroscopic findings. The skilled arthroscopist should obtain reliable results without requiring the use of an image intensifier. The procedure allows for accurate isometric anatomic positioning without the need for isometry or the use of a tensiometer. The procedure provides excellent immediate reproducible fixation and early aggressive range of motion and weight bearing without loss of fixation.

Figure 1:
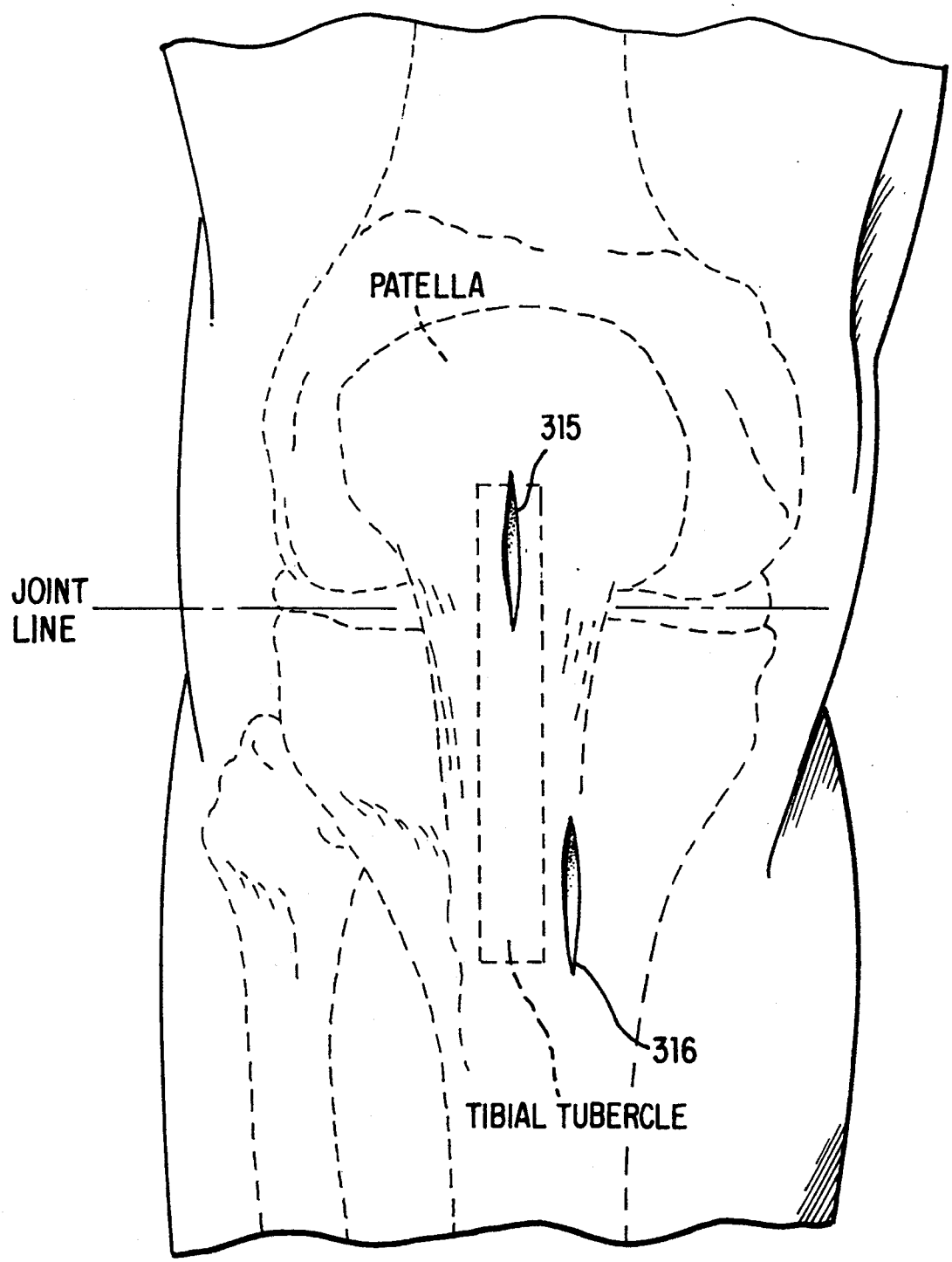
FIG. 1 is an illustration of the patella tendon bone area utilized in the bone plug and tendon graft preparation method with the incision locations shown.

Vertical incisions may be made on the patella and medial to the tibial tubercle that are approximately 2.5 cm in length as shown in FIG. 1. The skin incisions may be undermined in such a fashion as to provide sufficient mobility for retraction, while harvesting the patellar and tibial bone plugs. A carefully placed anteromedial incision 316 may begin approximately 1 cm medial to the tibial tubercle and 2 cm distal to the joint line, extending for 2.5 cm. The patella incision 315 may begin at the distal pole of the patella and extend approximately over the mid line of the patella for 2.5 cm. The tibial incision may be also used for placement of the tibial tunnel and subsequent fixation of the graft. Using vertical incisions has helped to prevent cases of intrapatellar contracture syndrome. Using this procedure, the morbidity ascribed to using a patellar tendon graft that has been reported by others has not been encountered.

Figure 2:
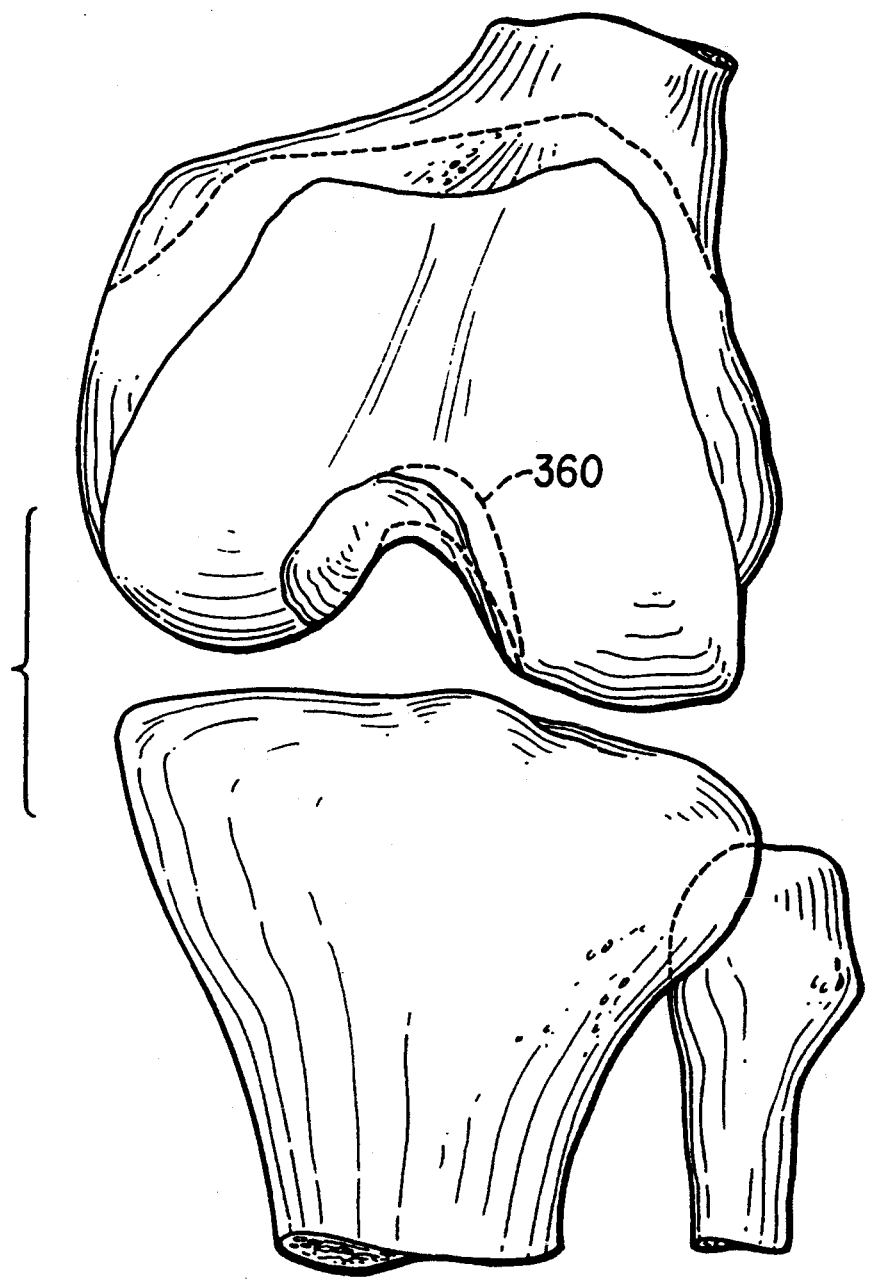
FIG. 2 is an illustration of the notchplasty contour utilized in the bone plug and tendon graft preparation method.

Arthroscopic diagnostic completion of all other procedures such as meniscectomy, meniscal repair, removal of loose bodies, debridement of anterior cruciate ligament tear, etc., may be accomplished without tourniquet control in order to allow sufficient time for the ACL reconstruction procedure. Notchplasty may be commenced under tourniquet control. The boundary of the notchplasty is shown as contour 360 in FIG. 2, and should be sufficiently wide (approximately 2 cm) and must be sufficiently posterior to include the posterior lateral femoral cortex in order to ensure accurate placement and subsequent isometricity.

Figure 3:
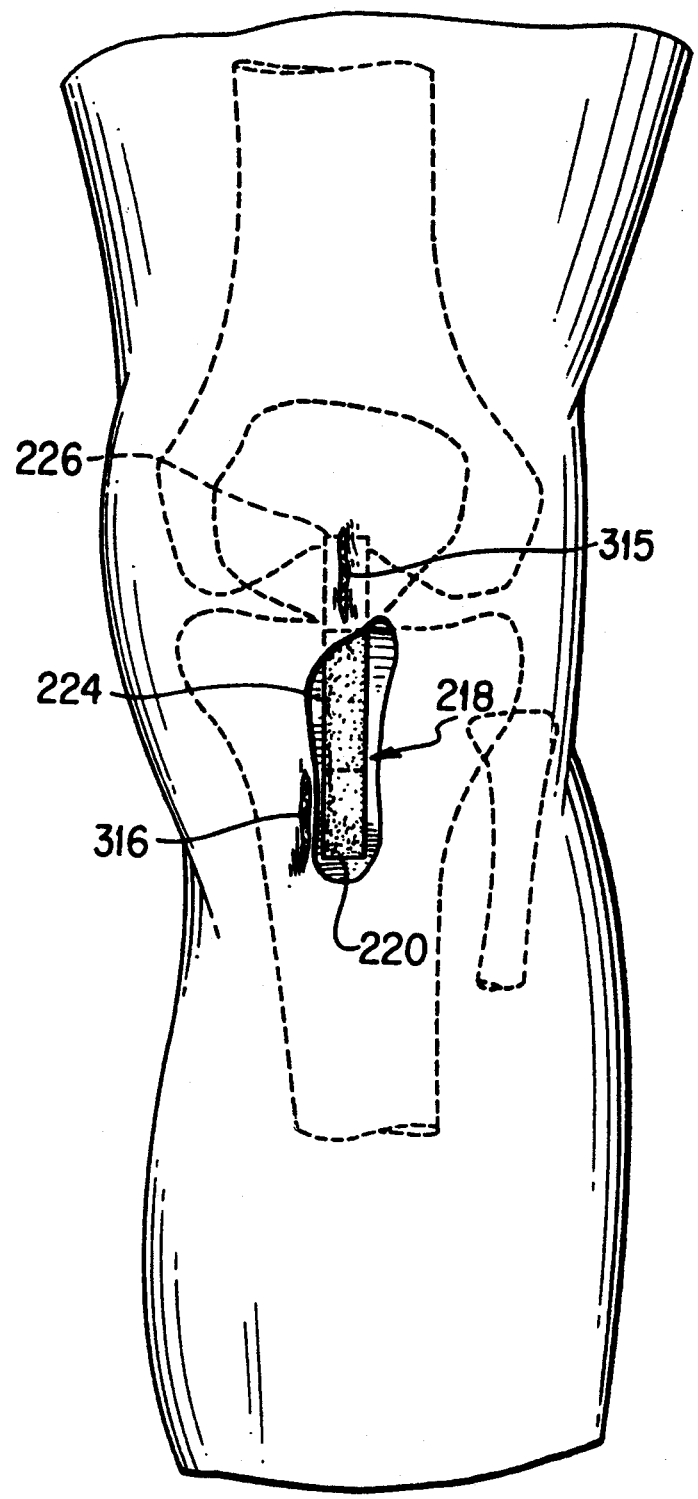
FIG. 3 depicts the site of the bone tendon bone autograft.
Figure 4:
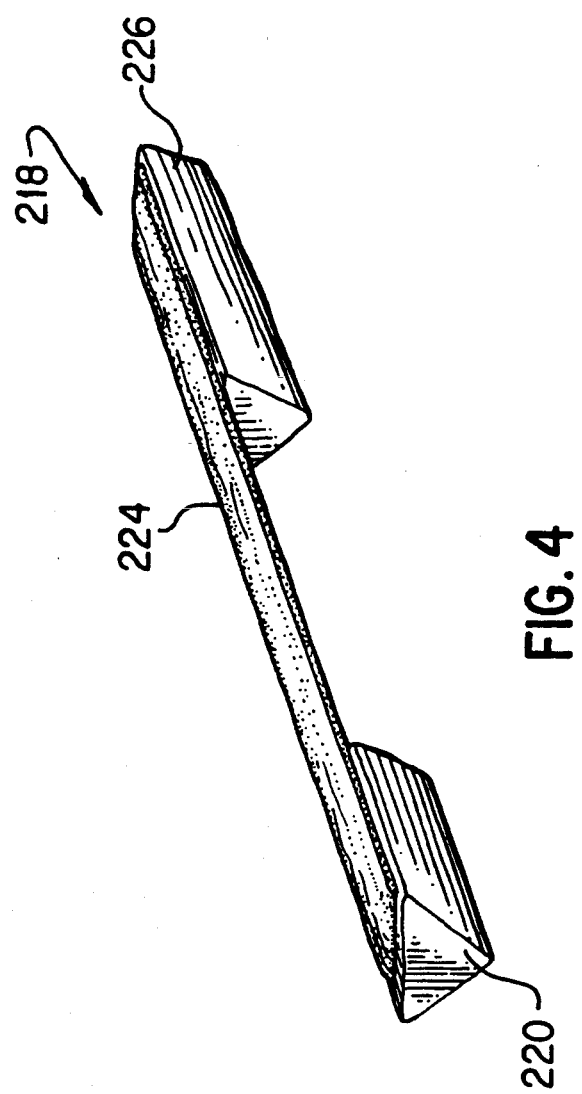
FIG. 4 is a perspective view of a bone-tendon-bone autograft harvested from FIG. 3.
Figure 15:
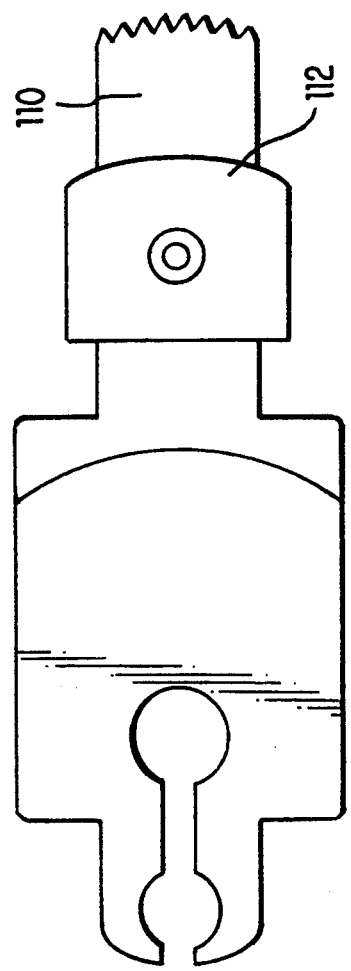
FIG. 15 is a side view of an oscillating saw blade invented by Dr. David McGuire.

A patellar tendon harvest 218, as shown in FIGS. 3 and 4, may be taken through the vertical incisions 315 and 316 and may be harvested with an oscillating saw. The presently preferred oscillating saw blade 110 and its use described herein are an invention of Dr. David McGuire illustrated in FIG. 15. The saw blade 110 gets mounted on a camshaft perpendicular to that camshaft. In operation, the camshaft rotates in a partial turn clockwise by a small angular distance and then rotates in a partial turn counterclockwise by an equal small angular distance. The camshaft rotates back and forth causing the saw blade to oscillate back and forth rapidly in the plane of the blade. In accordance with Dr. McGuire's invention, the cutting edge of the saw blade has a concave prob forming an arc on a circle centered on the camshaft's axis of rotation. Further, the invention in this embodiment includes a collared stop 112. The collared stop 112 has a stopping edge in the shape of an arc on a circle concentric with the circle coincident with the arc of the saw blade cutting edge. The presently preferred distance between the cutting edge and the stopping edge is 8 mm. The stop 112 uniformly limits the depth to which the saw blade can cut all along a cutting operation. Therefore a kerf (i.e., a cut) of uniform depth is obtained. A vertical edge at the end of the cut is formed by guiding the saw vertically down into the bone until the stop collar meets the bone. If desired, the portion of the sides of the saw blade lying between the cutting edge and the stop collar may be coincident with radii extending from the camshaft's axis of rotation. The sides are then normal to the cutting edge. Such a blade can make a vertical edge at the end of a cut all the way down to the bottom of the cut. Where as in the embodiment shown in FIG. 15, the arc of the cutting edge is a relatively small angular distance. The side are approximately normal to the cutting edge, and therefore permit cutting a substantially rectangular kerf.

The tibial tubercle portion 220 may be harvested first with a width of 10 mm. The initial cut is made by the oscillating saw vertically through the cortex and is then angled. By angling the cuts along both sides of the bone block, a V-shaped block may be formed. Preferably however, the angles are made at approximately 60° from horizontal and the transverse cut is also angled. An osteotome, or similar chisel device, is inserted in the transverse cut to pry out the bone block which will have a trapezoidal shape. The bottom surface is formed by a controlled fracture when the osteotome lifts the bone weakened by the angled cuts. It is particularly important that the cuts by the oscilating saw be placed precisely to avoid extending beyond the region of bone to be harvested, because the bone can be excessively weakened in that it becomes more susceptible to fracture. If a conventional oscillating saw is used, the kerf may not be of uniform depth along its length, nor might the opposing ends of the cut have vertical walls. Instead, the opposing ends will typically have a gradual taper to the full cut depth, a situation requiring that the kerf must extend beyond the region of the bone to be harvested, with the result of greater risk of fracture. However, by utilizing Dr. McGuire's design of oscillating saw described above, thekerf may have a uniform depth vertical and opposing ends, and thus provides a greatly reduced risk of fracture.

Figure 14A:
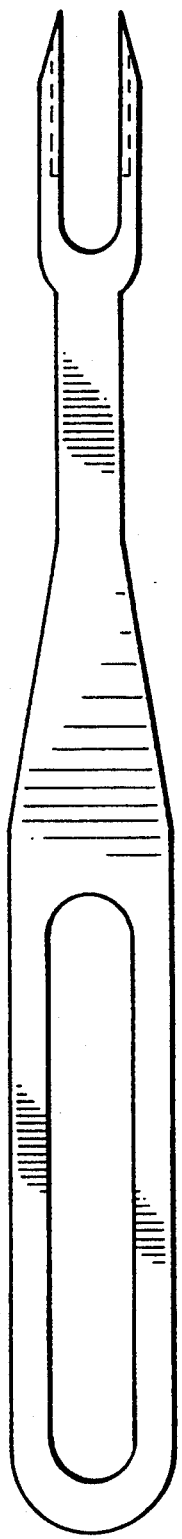
FIG. 14A is a plan view of a double bladed tendon harvester utilized in the bone plug and tendon graft preparation method of the present invention.
Figure 14B:
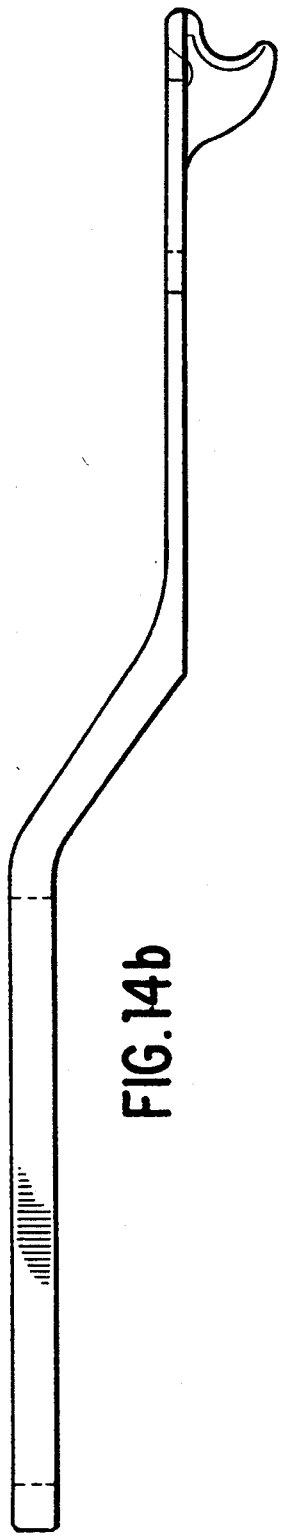
FIG. 14B is a side view of the double bladed tendon harvester of FIG. 14A.

After creating the bone block, the central one third portion 224 of the patellar tendon may be harvested using a Smillie meniscotome. It has been found to be preferable however to use a double bladed tendon harvester such as that shown in FIG. 14. The double bladed tendon harvester of FIG. 14 is the subject of a co-pending patent application Ser. No. 08/019,546 filed on the same date herewith. The disclosure of the tendon harvester patent application is hereby incorporated by reference herein. The double bladed tendon harvester assists in cutting a tendon graft of consistent width.

The patella bone portion 226 may be harvested with a width of approximately 11 mm with care taken to avoid the proximal portion of the patella and potential interruption of the quadriceps tendon insertion. Thus the patella bone plug 226 is the larger bone plug and the tibial tubercle bone plug 220 is the smaller bone plug. The precise widths and lengths can be varied according to the size of the patient. The double bladed tendon harvester locates the position for the bone cuts. A Bovee electrocautery device marks the bone for cutting. An oscillating saw is angled at approximately 60° and to a depth of about 8 mm. A horizontal saw cut is made 4–5 mm. distal to the proximal pole of the patella. An osteotome or similar device is used to pry up the bone block. The resultant trough of the patellar defect may be contoured with a rongeur and filled with bone chips removed in preparation of the graft.

Figure 5:
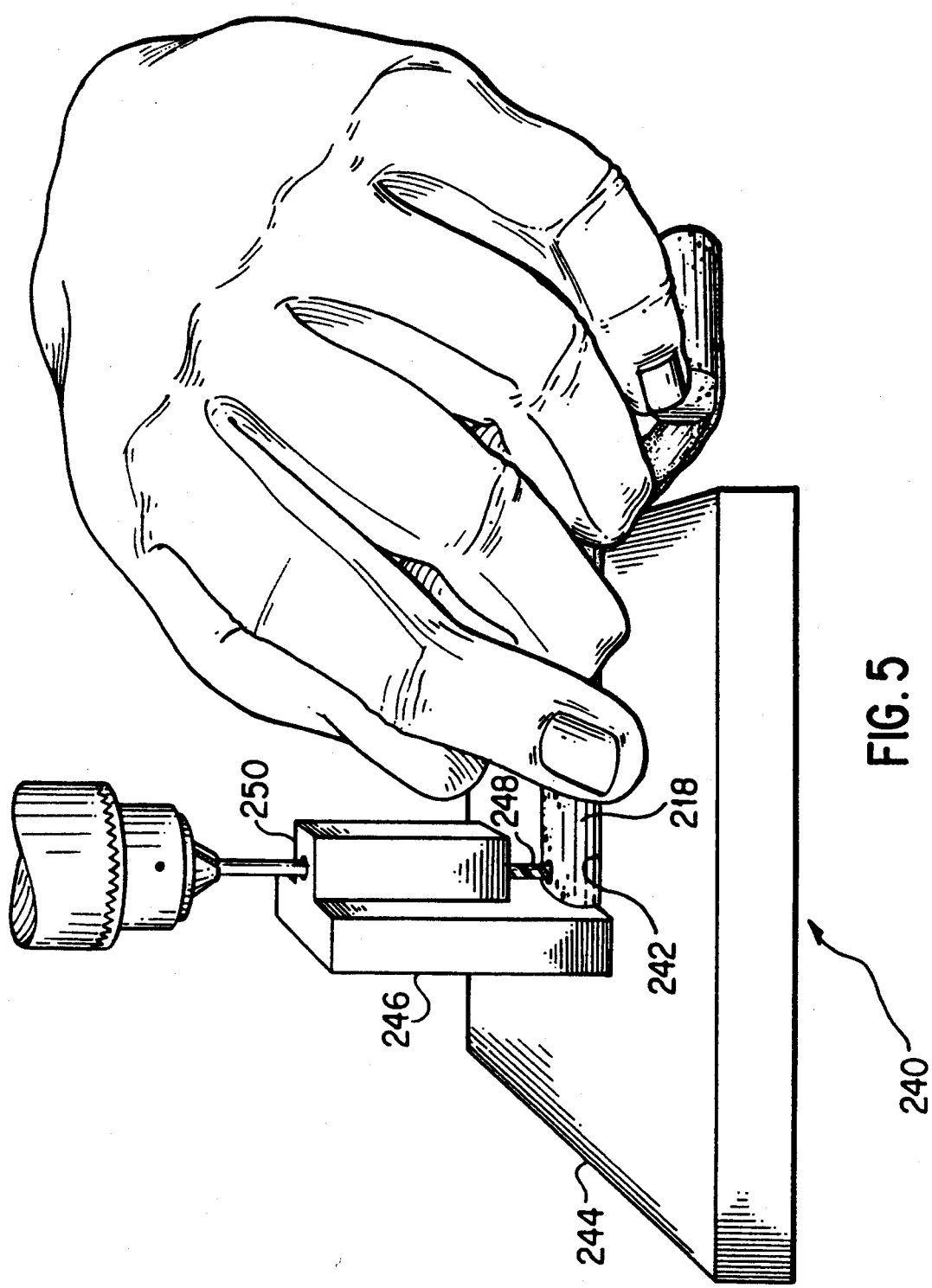
FIG. 5 depicts a drill guide of the present invention used for drilling a hole in the bone-tendon-bone autograft.

The graft may be prepared at a side table by removing any undesireable burrs or sharp edges with a rongeur. The prepared bone blocks of the graft approximate a trapezoidal shape. The graft 218 may be passed through an appropriate sizing cylinder 230 to ensure easy passage through an appropriately sized bone tunnel. The sizing cylinder 230 may be provided as a separate tube or on a bone block drill guide 10 of the present invention shown in FIG. 6a. A single hole embodiment of the bone block drill guide is shown in FIG. 5. A drill hole may be placed in the bone plugs of the graft using the drill guide 240 as shown in FIG. 5. The drill guide 240 includes a base 244 and a support tower 246. The support tower suspends a drill guide member 249 having a drill bit guide hole 250 therethrough. The base 244 includes a positioning station 242 into which the bone plugs of the graft may be placed when drilling holes in the bone plugs. The positioning station 242 is located directly beneath the drill guide member 249. In the presently preferred embodiment, the positioning station is a trough. In order to drill a hole in the bone plug, the drill bit 248 is inserted through the drill guide hole 250 down through to the bone plug where the hole is drilled. By pushing the bone plug up against the support tower 246, the drill hole can be made in a reproducible location a predetermined distance from the end of the bone plug.

A strong suture may be placed in the smaller bone plug and a flexible wire, preferably between 20 and 26 gauge, may be placed in the larger bone plug. The preferred embodiment of the bone block drill guide is shown in use in FIG. 7. In this embodiment, the drill guide 10 may include a guide member 300 which may be removable. The guide member 300 includes supports that are insertible into receiving holes 360 in the base. The bone-tendon-bone autograft 218 may be removably inserted into one of the various sized positioning stations 350. Again, the positioning stations are troughs in the illustrated embodiment. Thus, a first hole may be drilled into one of the bone blocks. Then the graft can be removed from the trough and the undrilled bone block can be inserted into a second trough corresponding to the size of the bone block. The drill guide member is moved into alignment with the second trough for drilling the next hole.

The guide member 300 includes a plurality of drill bit guide holes 340 so that the user may select from a number of different predetermined distances for the drilling of the hole in the bone plug. Also, more than one hole may be used for drilling more than one hole into the bone plug on occasion. It is noted that with reference to FIG. 7, the surgeon may hold onto the drill guide member 300 during the drilling procedure rather than needing to hold onto the bone plug itself. By pressing down on the drill guide member, the surgeon can contribute to holding the bone plug in place during drilling. The surgeon's fingers thus need not hold the bone plug directly and are kept away from the drilling action thereby reducing the risk of contact with the drill bit.

Figure 6A:
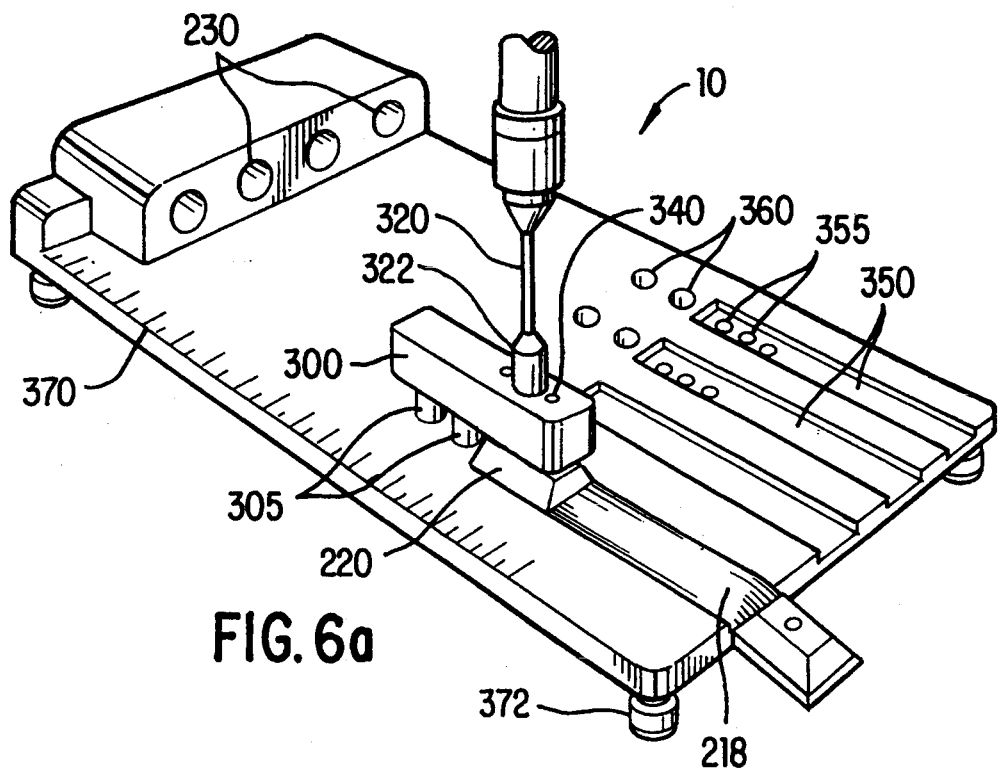
FIG. 6a is a perspective view of a presently preferred embodiment of a bone block drill guide of the present invention.

Referring now to FIG. 6a, a more detailed description of the bone block drill guide 10 can be made. The bone block drill guide advantageously includes a series of sizing cylinders 230 mounted on the base 370. Mounting the sizing cylinders on the base prevents them from getting lost or falling on the floor. Each of the sizing cylinders 230 may be for a different size. For example, these may include 9 mm, 10 mm, 11 mm and 12 mm cylindrical holes. By fixing the sizing cylinders on the base, it is easy to quickly locate the correctly sized cylinder. The surgeon does not need to rummage through a variety of individual separate cylinders. A bone plug in preparation may be slid through one of the sizing holes to verify that it is appropriately sized for the tunnel into which it will be inserted. If the bone plug has burrs or other protrusions preventing it from sliding through the sizing cylinder, the surgeon can use a rongeur to remove them.

Figure 6B:
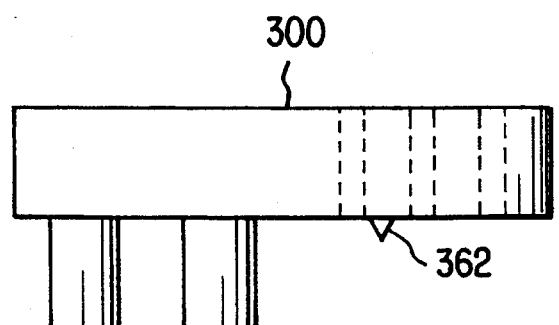
Figure 6C:
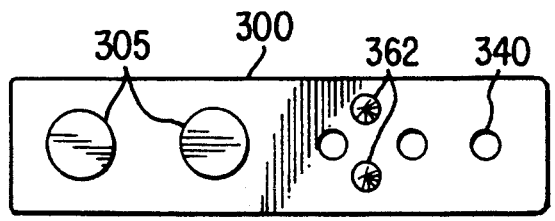

The base 370 is supported by four legs. Rubber tips 372 on the legs serve to cushion the bone block drill guide 10. The legs of the presently preferred embodiment are about one half inch in height. The legs and base of the presently preferred embodiment are integrally formed of a solid metal, such as stainless steel. The drill guide member 300 is supported by two support shafts 305. The support shafts 305 are proportioned in diameter to fit through the receiving holes 360 in the base 370 of the bone block drill guide. The support shafts 305 drop through the receiving holes 360. The shafts 305 are securely attached to the drill guide member 300. In the presently preferred embodiment, the shafts 305 and the drill guide member 300 are an integral structure made of a solid metal, such as stainless steel. The drill guide member 300 can thus be placed in alignment with any of the troughs 350. To perform a drilling operation the support shafts 305 are inserted into the receiving holes 360 which align the drill guide member 300 with the positioning station or trough of the appropriate width for receiving the bone plug. The shafts 305 maintain the drill guide member 300 in alignment with the positioning station or trough throughout the drilling operation. The drill guide member 300 is lifted off the base 370 to permit the bone plug to be inserted into the trough. The drill guide member 300 is then lowered onto the bone plug. The drill guide member 300 may be advantageously provided with protrusions for helping to secure the bone plug from moving during the drillng. In FIGS. 6b and 6c, the drill guide member is shown with two round pointed spikes 362 for slightly pricking the bone plug to hold it in place. The drill guide member is provided with three drill guide holes 340. Each trough 350 is provided with three drill receiving holes 355 which will align directly beneath the drill guide holes 340 when the drill guide member 300 is aligned with the respective trough.

The drill bit 320 may be provided with a stop 322 to limit the depth to which the drill bit can be inserted through the drill guide. The drill bit 320 preferably extends out from the stop 322 a length that will terminate at the middle of the base 370 when the stop contacts the top of the drill guide member 300. The stop may be formed by a fixed or adjustable collar or simply by a weld spot on the drill bit. Because the drill bit will not be forced beyond the middle of the base 370, the drill receiving holes 355 do not necessarily have to exit through the bottom of the base 370. However, a completely open hole is preferred for easier cleaning and more assurance that the drill bit will not contact the base. The receiving holes 355 are of a larger diameter than the drill bit guide holes 340. The drill bit guide holes are preferably 3/32 of an inch, while the receiving holes 355 are slightly larger than that. The receiving holes permit the drill bit to go through the bone without being contaminated by a surface supporting the bone from underneath.

The bone plug is pushed up against the end of a positioning station or trough. The consistent positioning of the bone plug permits accurate drilling of the holes. Different hole positions on the bone block are achieved by selecting from among the three guide holes in the drill guide member 300. In accordance with an alternate embodiment of the bone block drill guide shown in FIG. 8, the support tower 12 straddles a trough 50. The support tower 12 suspends a drill guide member 14 above the trough 50. The drill guide member 14 has a drill guide hole 40 therethrough. Aligned with the drill guide hole 40 is a hole 55 in the trough 50. The hole may go through the entire base 70 or the base 70 may be made sufficiently thick and the hole 55 sufficiently deep so that the drill bit does not scrape any base material during drilling. The support tower 12 has a tunnel 16 through its bottom aligned with the trough 50. The tunnel 16 is high enough to permit a bone block to fit therethrough. A stop clip 18 is included with the support tower 12 to provide different end positions in the trough against which the bone block will butt up against. With the stop clip pulled away from the support tower 12 the tunnel 16 is open. In this position, the bone block may be inserted through the tunnel against the end of the trough 50. Alternatively, the stop clip 18 can be pushed against the support tower 12 to close the tunnel 16.

Figure 9:
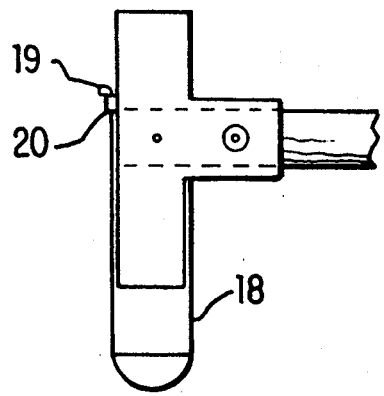
FIG. 9 is a plan view of the bone block drill guide of FIG. 8. With the stop clip in the open position.
Figure 10:
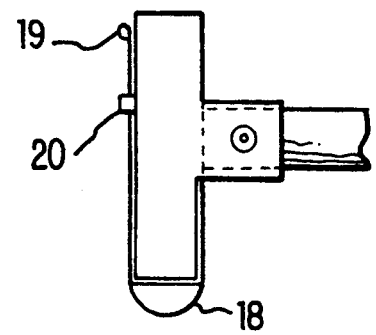
FIG. 10 is a plan view of the bone block drill guide of FIG. 8 with the stop clip in the closed position.

As shown in FIG. 9, a flange 19 at the end of the stop clip 18 abuts a keeper 20 secured to the support tower 12. The keeper 20 may provide a loop or slot through which the stop clip 18 may slide. The keeper 20 also serves to keep the stop clip from coming off the support tower. In the open position, the bone block may be inserted through the tunnel 16 against the end of the trough 50 for performing the drilling operation. An alternate hole location may be achieved by pushing the stop clip up against the support tower 12 thereby closing off the tunnel 16. When the bone block is inserted into the trough it can be pushed no further than up against the stop clip 18 as in the position shown in FIG. 10. In this position a hole closer to the end of the bone plug may be drilled. A pull tab 22 may be provided on the stop clip 18 to make pulling the stop clip easier to handle.

An alternative to the sliding stop clip would be a removable slot cover. The slot cover would fit around the support tower to block the tunnel 16. The slot cover could be removed thereby making for easier cleaning. Spring steel may be used for the slot cover or the stop clip. The presently preferred dimensions would be to have the support tower extend nine millimeters in depth. The drill bit guide hole 40 is five millimeters from the nearest face of the support tower 12. Thus with the stop clip 18 in the closed position, holes are drilled five millimeters from the end of the bone plug. With the stop clip removed and the tunnel 16 open, the hole is drilled in the bone plug 14 millimeters from its end.

Figure 7:
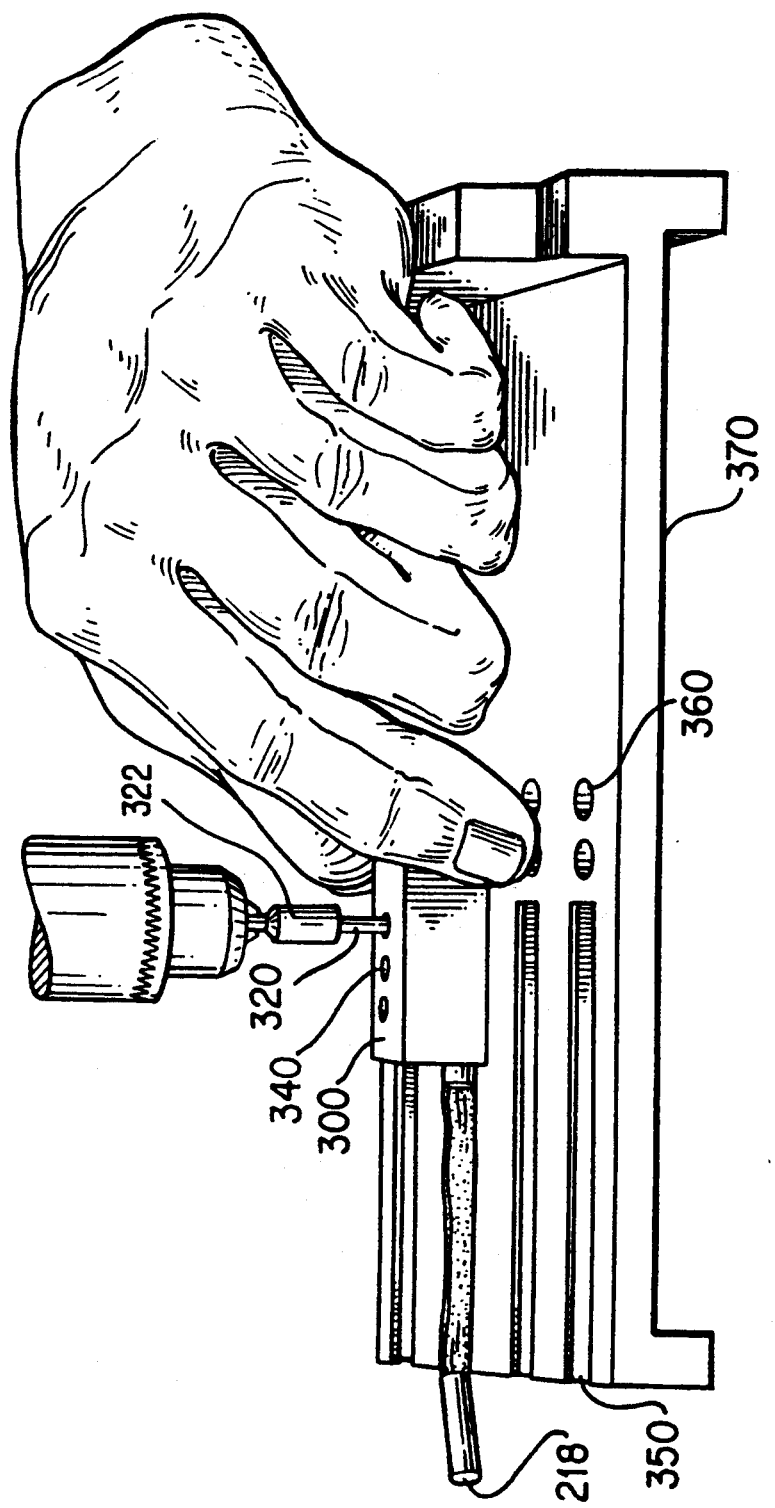
FIG. 7 depicts the bone block drill guide of FIG. 6 being used for drilling a hole in the bone-tendon-bone autograft.
Figure 8:
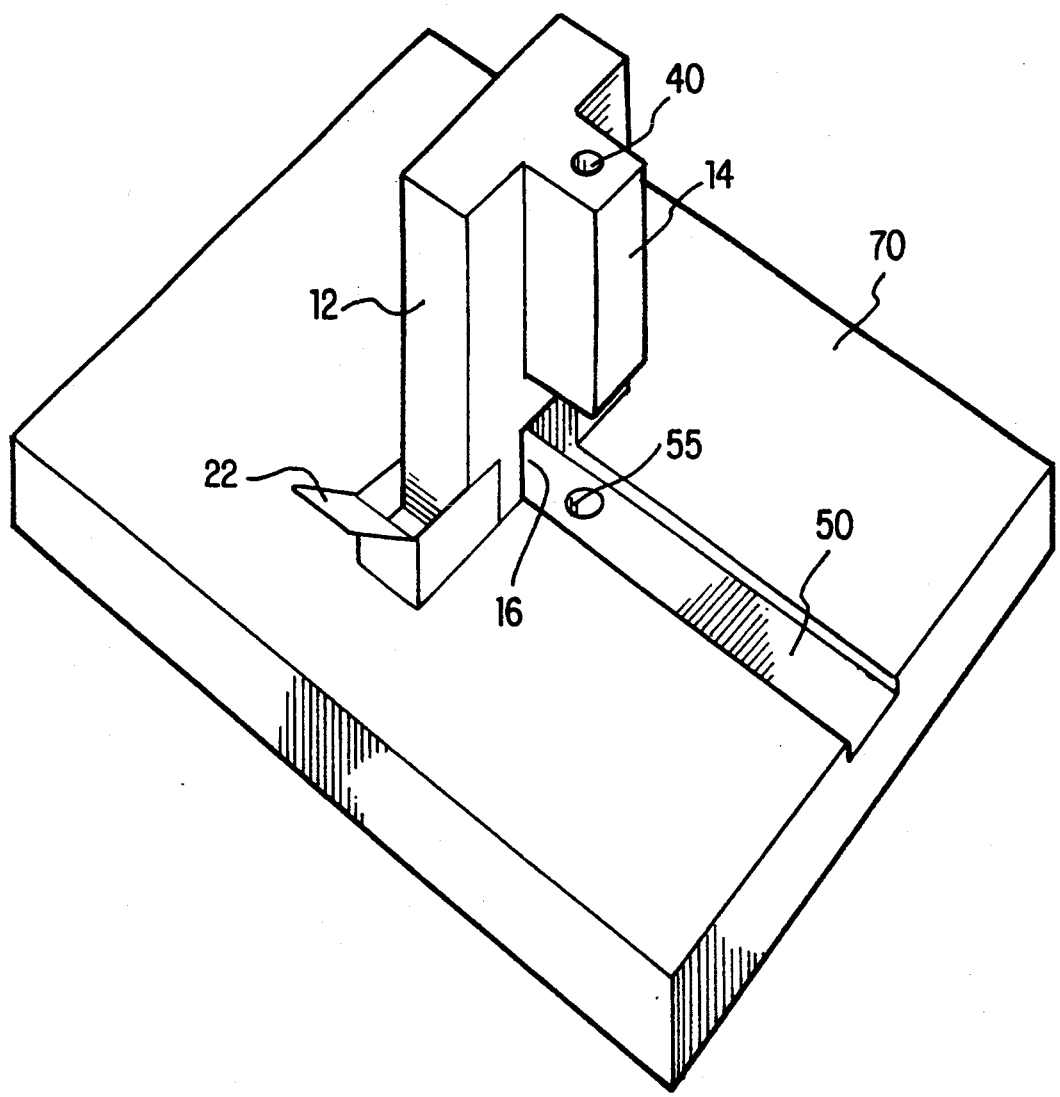
FIG. 8 is an alternate embodiment of the drill guide of the present invention.
Figure 11:
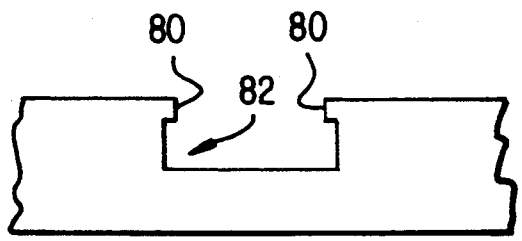
FIG. 11 is an end view of an alternate design for a trough in the bone block drill guide.

The original troughs shown in FIGS. 6a, 7 and 8 are preferably rectangular in cross section, three millimeters in depth with any of a variety of widths from nine millimeters to twelve millimeters wide. An alternate proposed trough design is shown in end view in FIG. 11. The trough of FIG. 11 is designed for receiving an insert for forming the bottom surface of the trough. In this manner, alternate shapes may be provided for the bottom surface of the trough or the single trough may be used to accommodate all different trough widths. The sidewalls 80 at the top of the trough in FIG. 11 are three millimeters deep and twelve millimeters apart. Beneath these side walls is a widened channel 82 for receiving a bottom surface insert.

Figure 12C:
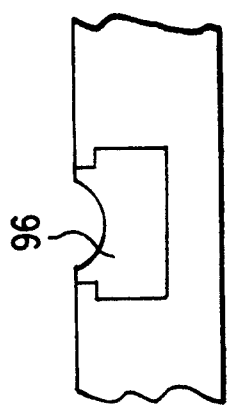
FIGS. 12A, 12B, 12C, 12D and 12E are end views of the trough of FIG. 11 having different base inserts therein.
Figure 12B:
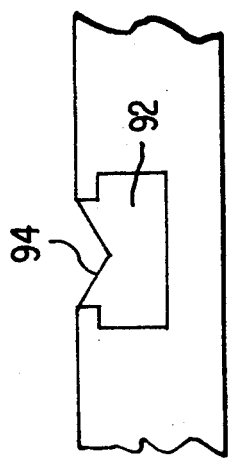
Figure 12A:
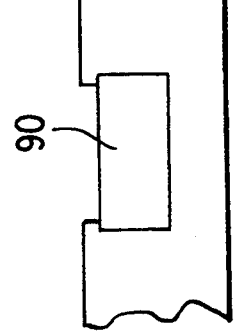
Figure 12E:
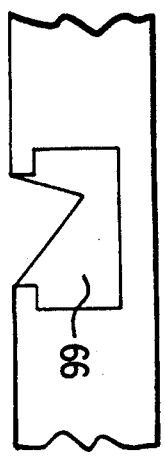
Figure 12D:
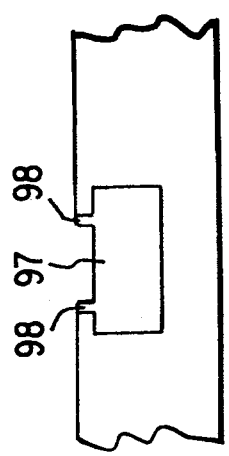

FIGS. 12A-E illustrate a variety of bottom surface inserts. In FIG. 12A a rectangular insert 90 emulates the original trough design. In FIG. 12B, the bottom surface insert 92 has a V shaped notch 94 throughout its length. The V shaped notch bottom surface allows for graft drilling at 90 degree rotation to the original. In FIG. 12C a half moon bottom surface insert 96 is provided. The arcuate bottom surface of FIG. 12C allows for drilling at any axis dependent on the match between the arc radius of the trough and sculptured contour of the bone plug. In FIG. 12D, the bottom surface insert 97 emulates the original rectangular trough with a narrower width. This bottom surface insert is a rectangular cylinder with two side walls 98 sticking up therefrom for sliding up along the sidewalls of the receiving trough. Thus the single receiving trough can be used with a variety of bottom surface inserts to provide rectangular troughs of any of a number of widths. FIG. 12E, illustrates a right hand V notch insert 99. Alternatively, the notch may be provided on the other side to give a left handed v notch insert. Because of the irregular shape of the bone plug, the various v notches may be used to more conveniently orient the bone plug to achieve the desired horizontally oriented hole.

Figure 13:
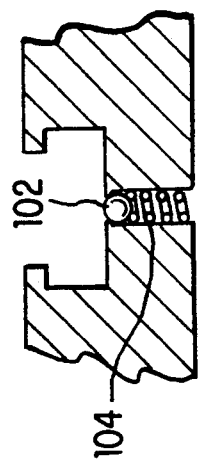
FIG. 13 is a cross sectional view of an alternate trough of the type shown in FIG. 11.

Various methods may be used to lock the bottom surface insert into position. One method would be to provide a set screw through a threaded hole in the bottom of the base plate. The screw would lock the bottom surface insert in place. Another arrangement is shown in FIG. 13. A ball bearing 102 may be suspended on a spring 104 in a hole beneath the receiving channel 82. Each bottom surface insert may be provided with a correspondingly shaped groove into which the ball would be pushed when the bottom surface insert is in place within the receiving channel 82. Thus, the bottom surface insert would be held in place by the spring loaded ball bearing. However it would be possible to simply slide the bottom surface insert out of position by using enough force to overcome the spring loaded ball. To facilitate removal of a bottom surface insert using the spring loaded ball bearing system, a notch may be taken out of the base plate beneath the receiving channel 82. The notch would permit a thumb to hold up against the bottom of the bottom surface insert while another finger holds the insert from the top. To make the grip easier the bottom of the bottom surface insert may be knurled to prevent the thumb on the bottom surface from slipping. The thumb and finger can be used to pull the bottom surface insert out from the receiving channel 82. The thumb and forefinger grip would provide for easy insertion and removal.

Of course, it should be understood that various changes and modifications to the preferred embodiments described above will be apparent to those skilled in the art. For example, the tower or shafts connected to the drill guide member may be either fixed to the base or readily removable and adjustable on the base. Instead of using troughs as positioning stations to hold a bone block in place, vertical studs on a flat base plate may be arranged so that the bone block is placed between two sets of vertical studs. The bone blocks may be completely cut out of the bone or a prying action can be used to remove the bone block after initial cuts have been made. These and other changes can be made without departing from the spirit and scope of the invention and without diminishing its attendant advantages. It is therefore intended that such changes and modifications be covered by the following claims.

What is claimed is:

1. A bone block drill guide for use in drilling a hole in a bone block comprising:
   a base plate having a plurality of troughs of different widths, each of the troughs having a bottom surface with at least one hole therein and dimensions suitable for receiving a bone block therein;
   a drill guide member having at least one hole therethrough for alignment with the at least one hole in the bottom surface of one of the troughs; and
   means, adjustably mountable on said base plate, for aligning said drill guide member over said one of the troughs.

2. The bone block drill guide of claim 1 further comprising means for adjusting a distance between the at least one hole in a trough and an end wall found in the trough when said drill guide member is aligned with the trough.

3. The bone block drill guide of claim 2 wherein said adjusting means comprises a stop clip which forms the end wall when inserted across the trough.

4. The bone block drill guide of claim 3 wherein said means for aligning has a tunnel therethrough so as to permit access through said one of the troughs to an end wall said one of the troughs formed in said base plate and wherein said stop clip blocks off access through the tunnel when inserted across the trough.

5. The bone block drill guide of claim 1 wherein said base plate includes a plurality of holes, each individually aligned with one of the troughs and wherein said means for aligning comprises a plurality of shafts attached to said drill guide member for insertion into the holes of said plurality of holes that are in alignment with said one of the troughs.

6. The bone block drill guide of claim 1 further comprising protrusion extending from an underside of said drill guide member, said protrusions serving to assisting in holding a bone block in place within said one of the troughs during drilling.

7. The bone block drill guide of claim 1 further comprising a plurality of sizing cylinders mounted on said base plate, each of said sizing cylinders having a different inner diameter.

8. A bone block drill guide comprising:
   a base plate having a trough end wall, a pair of oppositely facing trough side walls and a channel beneath an area between the side walls for receiving a trough bottom surface insert, the bottom surface insert having at least one hole therein;
   a drill guide member having at least one hole therethrough for alignment with the at least one hole in the bottom surface insert received within the channel; and
   means for aligning said drill guide member over the trough bottom surface insert received in the channel.

9. The bone block drill guide of claim 8 further comprising means for blocking access between the trough side walls to the trough end wall.

10. The bone block drill guide of claim 8 wherein said means for aligning has a slot therethrough so as to permit access to the trough end wall and wherein a stop clip slidably mounted to said support means blocks off access to the trough end wall when slid in position across the slot.

11. The bone block drill guide of claim 8 further comprising means for securing the trough bottom surface insert in the channel.

12. The bone block drill guide of claim 11 wherein said securing means comprises a spring loaded ball mounted in a hole in a bottom of said base plate beneath the channel and a groove in an underside of the trough bottom surface insert for engaging the spring loaded ball.

13. The bone block drill guide of claim 8 wherein said base plate includes a plurality of holes aligned with the channel and wherein said means for aligning comprises a plurality of shafts attached to said drill guide member for insertion into the plurality of holes.

14. The bone block drill guide of claim 8 further comprising a plurality of sizing cylinders mounted on said base plate, each of said sizing cylinders having a different inner diameter.

15. A bone block drill guide comprising:
   a base plate having at least one trough therein, the at least one trough having a bottom surface with at least one hole therein;
   a plurality of sizing cylinders mounted on said base plate, each of said sizing cylinders having a different inner diameter;
   a drill guide member having at least one hole therethrough for alignment with the at least one hole in the bottom surface of the at least one trough; and
   means, connected to said drill guide member, for aligning said drill guide member over the at least one trough.

16. The bone block drill guide of claim 15 wherein said means for aligning comprises a tower mounted on said base plate so as to suspend said drill guide member over the at least one trough.

17. The bone block drill guide of claim 15 wherein said base plate includes a plurality of holes aligned with the at least one trough and wherein said means for aligning comprises a plurality of shafts for insertion into the holes to align said drill guide member with the at least one trough.

* * * * *